United States Patent [19]

Nestor et al.

[11] 4,419,347
[45] * Dec. 6, 1983

[54] NONAPEPTIDE AND DECAPEPTIDE ANALOGS OF LHRH, USEFUL AS LHRH ANTAGONISTS

[75] Inventors: John J. Nestor, San Jose; Gordon H. Jones; Brian H. Vickery, both of Cupertino, all of Calif.

[73] Assignee: Syntex (U.S.A.) Inc., Palo Alto, Calif.

[*] Notice: The portion of the term of this patent subsequent to Nov. 18, 1997 has been disclaimed.

[21] Appl. No.: 366,635

[22] Filed: Apr. 8, 1982

Related U.S. Application Data

[63] Continuation of Ser. No. 194,180, Oct. 6, 1980, Pat. No. 4,341,767.

[51] Int. Cl.³ .................. A61K 37/00; C07C 103/52
[52] U.S. Cl. .................. 424/177; 260/112.5 LH
[58] Field of Search .............. 260/112.5 LH; 424/177

[56] References Cited

U.S. PATENT DOCUMENTS

| | | | |
|---|---|---|---|
| 4,234,571 | 11/1980 | Nestor et al. | 260/112.5 LH |
| 4,318,905 | 3/1982 | Nestor et al. | 260/112.5 LH |
| 4,341,767 | 7/1982 | Nestor et al. | 260/112.5 LH |

*Primary Examiner*—Delbert R. Phillips
*Attorney, Agent, or Firm*—James M. Kanagy; Tom M. Moran

[57] ABSTRACT

Nonapeptide and decapeptide analogs of LHRH which have the formula

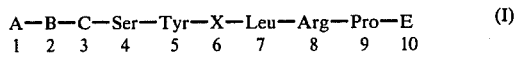

and the pharmaceutically acceptable salts thereof, wherein:

X is a D-alanyl residue wherein one hydrogen on C-3 is replaced by:
  (a) a carbocyclic aryl-containing radical selected from the group consisting of phenyl substituted with three or more straight chain lower alkyl groups, naphthyl, anthryl, fluorenyl, phenanthryl, biphenylyl and benzhydryl; or
  (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or
  (c) a heterocyclic aryl containing radical selected from the group consisting of radicals represented by the following structural formulas:

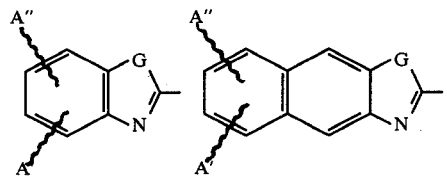
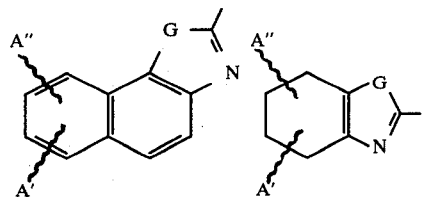
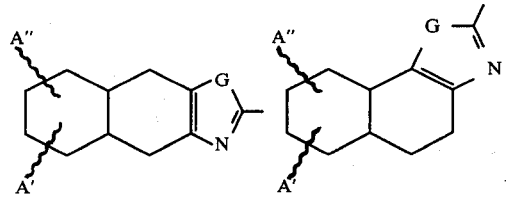

wherein

A" and A' are independently selected from the group consisting of hydrogen, lower alkyl, chlorine, and bromine, and G is selected from the group consisting of oxygen, nitrogen, and sulfur;

A is an aminoacyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, and N-acyl-X wherein X is as defined previously;

B is an amino acyl residue selected from the group consisting of D-phenylalanyl, D-p-halophenylalanyl, 2,2-diphenylglycyl, and X wherein X is as defined previously;

C is an amino acyl residue selected from the group consisting of L-tryptophanyl, D-tryptophanyl, D-phenylalanyl and X wherein X is as defined above;

E is glycinamide or —NH—$R^1$, wherein $R^1$ is lower alkyl, cycloalkyl, fluoro lower alkyl or

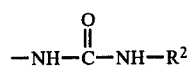

wherein $R^2$ is hydrogen or lower alkyl;

are disclosed. These compounds are LHRH antagonists.

28 Claims, No Drawings

NONAPEPTIDE AND DECAPEPTIDE ANALOGS OF LHRH, USEFUL AS LHRH ANTAGONISTS

This is a continuation of application Ser. No. 194,180, filed Oct. 6, 1980, now U.S. Pat. No. 4,341,767 issued 7/27/82.

BACKGROUND OF THE INVENTION

Luteinizing hormone (LH) and follicular stimulating hormone (FSH) are released from the anterior pituitary gland under the control of the releasing hormone LHRH produced in the hypothalamic region. LH and FSH act on the gonads to stimulate the synthesis of steroid hormones and to stimulate gamete maturation. The pulsatile release of LHRH, and thereby the release of LH and FSH, controls the reproductive cycle in domestic animals and humans.

LHRH also effects the placenta, and the gonads indirectly, in causing the release of chorionic gonadotropin (hCG).

Antagonists of LHRH are useful for the control of fertility. Such antagonists block ovulation in the female and suppress spermatogenesis in the male. Related to these effects is a suppression of normal circulating levels of sexual steroids of gonadal origin, including reduction in accessory organ weight in the male and the female. In domestic animals this effect promotes weight gain in a feed-lot situation, stimulates abortion in pregnant animals and in general, acts as a chemical sterilant.

The natural hormone releasing hormone LHRH is a decapeptide comprised of naturally occuring amino acids (which have the L-configuration except for the achiral amino acid glycine). Its sequence is as follows:

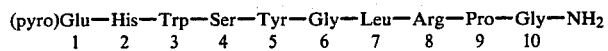

Many analogs of this natural material have been studied and the very large majority of them have proven to be of insufficient biological activity to be clinically useful. Certain select modifications have proven to have an agonist effect on biological activity. By far the most significant enhancement is obtained by changing the 6-position residue from Gly to a D-amino acid.

In addition to agonists, analogs have been prepared with are competitive antagonists to LHRH; all of which require deletion or replacement of the histidine residue at position 2; Vale, W., et al, *Science,* 176: 933 (1972). In general, it appears that a D-amino acid placed in the sequence at that position gives the best activity; Rees, R. W. A., et al, *J. Med. Chem.* 17: 1016 (1974).

It has also been shown that adding a modification at the 6 position, which, without the modification at position 2, results in the agonist activity cited above, enhances the antagonist activity of the 2-modified analogs; Beattie, C. W., et al, *J Med. Chem.,* 18: 1247 (1975); Rivier, J., et al, *Peptides* 1976 p. 427, Editions de l'Universite de Bruxelles, Belgium (1976).

Against the background of these two major alterations, which result in a potent series of LHRH antagonists; additional increments in antagonist activity may be had by modifying positions 1, 3 and/or 10 in the already 2, 6 modified peptide. Coy, D. H., et al *Peptides* 1976, p. 462, Editions de l'Universite de Bruxelles, Belgium (1976); Rivier, J. E., et al, *Life Sci.* 23: 869 (1978); Dutta, A. S., et al, *Biochem. Biophys. Res. Commun.* 81: 382 (1978), Humphries, J., et al, *Biochem. Biophys. Res. Commun.,* 85: 709 (1978). It has also been shown that N-acylation of the amino acid at position 1 is helpful; Channabasavaiab, K., et al, *Biochem. Biophys. Res. Commun.* 81: 382 (1978); Coy, D. H., et al, *Peptides.—Structure and Biological Function* p. 775, Pierce Chemical Co. (1979).

Since antagonists function by competing with LHRH for the appropriate receptors, high dosages of these compounds are required in order to block out the natural peptide. It is especially desirable, in view of this, to obtain antagonists with a very high degree of potency. The presently known set of analogs requires comparatively high levels of compound, with the attendant problems of increased possibility for toxicity and other side effects.

Therefore, there is a need to prepare antagonists of LHRH which have an even higher degree of biological activity than those heretofore described, and which can safely be used clinically in animals and humans.

SUMMARY OF THE INVENTION

The present invention refers to novel, highly potent nonapeptide and decapeptide analogs of LHRH in which a replacement at position 2, (thus converting the peptide to the antagonist series) is made more effective by replacement of the glycine residue at position 6 by one of a series of D-lipophilic amino acids which have carbocyclic or heterocyclic side chains, and which do not occur in nature. Further enhancements by substitutions at 1, 3 and/or 10 are also disclosed. The invention is also directed to various methods of use of these compounds and to pharmaceutical compositions therefore. A further aspect of the invention involves processes for the preparation of the novel compounds described above.

DETAILED DESCRIPTION OF THE INVENTION

Description of the Analogs

The present invention relates to novel nonapeptide and decapeptide derivatives of LHRH, of the formula:

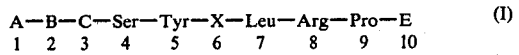

and the pharmaceutically acceptable salts thereof, wherein:

X is a D-alanyl residue wherein one hydrogen on C-3 is replaced by:
  (a) a carbocyclic aryl-containing radical selected from the group consisting of phenyl substituted with three or more straight chain lower alkyl groups, naphthyl, anthryl, fluorenyl, phenanthryl, biphenylyl and benzhydryl; or
  (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl, and adamantyl; or (c) a heterocyclic aryl containing radical selected from the group consisting of radicals represented by the following structural formulas:

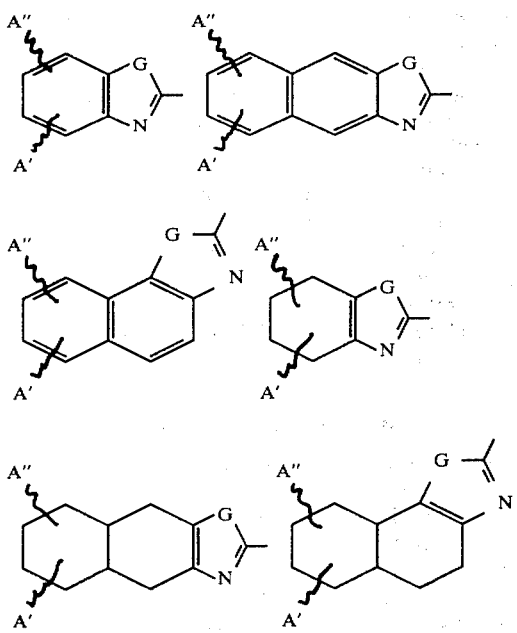

wherein A" and A' are independently selected from the group consisting of hydrogen, lower alkyl, chlorine, and bromine, and G is selected from the group consisting of oxygen, nitrogen, and sulfur;

A is an aminoacyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, and N-acyl-X, wherein X is as defined previously;

B is an amino acyl residue selected from the group consisting of D-phenylalanyl, D-p-halophenylalanyl, 2,2-diphenylglycyl, and X, wherein X is as defined previously;

C is an amino acyl residue selected from the group consisting of L-tryptophanyl, d-tryptophanyl, D-phenylalanyl and X, wherein X is as defined above;

E is glycinamide or —NH—R$^1$, wherein R$^1$ is lower alkyl, cycloalkyl, fluoro lower alkyl or

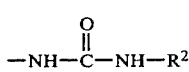

wherein R$^2$ is hydrogen or lower alkyl. The replacement of the L-histidyl residue which is at position 2 in LHRH with one of the residues herein specified is a requirement to convert the peptide to an LHRH antagonist. The replacement of the glycyl residue at position 6 in LHRH with one of the residues specified as X gives a dramatic enhancement of the antagonist effect. The substitutions disclosed herein at positions 1, 3 and 10 are further helpful in enhancing the antagonist activity.

Abbreviations and Definitions

As set forth above, and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972). These represent L-amino acids, with the exception of the achiral amino acid glycine, and with the further exception of any unnatural or natural amino acids which are achiral, or are otherwise designated as D-, and of those amino acids which are substituted herein into positions 1, 2, 3, 6 and 10 for those normally found in LHRH. All peptide sequences mentioned herein are written according to the generally accepted convention whereby the N-terminal amino acid is on the left and the C-terminal amino acid is on the right.

The abbreviation "NAc," when used as a prefix to an amino acid residue refers to an N-acyl amino acid residue.

Certain other abbreviations will be useful in describing the invention. The present invention employs replacements by amino acids which do not occur in nature. Particularly commonly employed among these are the following:

| Amino acid residue | Abbreviation |
|---|---|
| 3-(1-naphthyl)-D-alanyl | D-Nal(1) |
| 3-(2-naphthyl)-D-alanyl | D-Nal(2) |
| 3-(p-halophenyl)-D-alanyl | D-p-halo-Phe |
| 3-(p-fluorophenyl)-D-alanyl | D-p-F—Phe |
| 3-(p-chlorophenyl)-D-alanyl | D-p-Cl—Phe |
| 3-(p-bromophenyl)-D-alanyl | D-p-Br—Phe |
| 3-(2,3,4,5,6-pentamethylphenyl)-D-alanyl | D-Me5Phe |
| 3-(2,4,6-trimethylphenyl)-D-alanyl | D-TMP |
| 3-(benzimidazol-2-yl)-D-alanyl | D-BIA |
| 3-(4,5,6,7-tetrahydrobenzimidazol-2-yl)-D-alanyl | D-TBA |

Other residues employed herein are 2,2-diphenylglycyl, abbreviated DPG, and

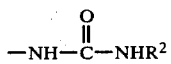

wherein R$^2$ is hydrogen or lower alkyl, abbreviated AzaGlyNHR, and the group -NHCH$_2$CH$_3$, abbreviated —NHEt.

As a further convenience, since the amino acid sequence of LHRH has been shown to be

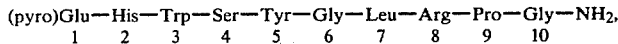

nona-and decapeptides in which the amino acid residues at particular places in the sequence have been replaced by other amino acid residues or other moieties are abbreviated by showing the nature of the substitution, superscribed by the location, followed by LHRH as the parent.

Thus, for example, the sequence,

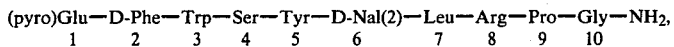
1   2   3   4   5   6   7   8   9   10 in which the Gly at position 6 has been replaced by D-Nal(2) and the His at position 2 has been replaced by D-Phe, is represented (D-Phe², D-Nal(2)⁶)LHRH; and the sequence

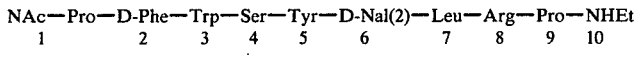
1   2   3   4   5   6   7   8   9   10 is represented:

(NAc-Pro¹, D-Phe², D-Nal(2)⁶, -NHEt¹⁰)LHRH.

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N, N'-dibenzylethylene-diamine or ethylenediamine; or (c) combinations, of (a) and (b), e.g., a zinc tannate salt and the like.

As used herein the term "lower alkyl" refers to a straight or branched chain saturated hydrocarbon group having from 1 to 4 carbon atoms such as, for example, methyl, ethyl, n-propyl, isopropyl, n-butyl, isobutyl, sec-butyl and tert-butyl; the term "cycloalkyl group" refers to a cyclic saturated hydrocarbon group having from 3 to 6 carbon atoms, for example cyclopropyl, cyclobutyl, cyclopentyl and cyclohexyl; the term "fluoro lower alkyl" refers to a lower alkyl group wherein one or more hydrogen atoms are replaced by fluorine, such as, for example, trifluoromethyl, pentafluoroethyl, 2,2,2-trifluoroethyl, and the like.

As used herein "naphthyl" is inclusive of 1- and 2-naphthyl; "anthryl" is inclusive of 1-, 2- and 9-anthryl; "fluorenyl" is inclusive of 2-,3-,4- and 9-fluorenyl; "phenanthryl" is inclusive of 2-,3-, and 9- phenanthryl; and "adamantyl" is inclusive of 1- and 2-adamantyl.

An "N-acyl" amino acid residue is an amino acid residue in which the amino nitrogen is bound in an amide linkage to a carboxylic acid residue; said carboxylic acid residue being that of a lower alkyl carboxylic acid or of benzoic acid.

Preferred Embodiments of the Compounds

Compounds which are preferred embodiments of the present invention are those wherein:

A is selected from the group consisting of L-(pyro)-Glu, D-(pyro)Glu, NAc-D-Phe, NAc-D-Nal(1), NAc-D-Nal(2), NAc-D-p-halo-Phe, NAc-D-Me5-Phe, NAc-D-TMP, NAc-D-BIA, NAc-D-TBA, and NAc-L-Pro;

B is selected from the group consisting of D-Phe, D-p-Cl-Phe and DPG;

C is selected from the group consisting of L-Trp, D-Trp, D-Phe, D-Nal(1), D-Nal(2), D-p-halo-Phe, D-Me5Phe, D-TMP, D-BIA and D-TBA;

X is selected from the group consisting of D-Nal(1), D-Nal(2), D-p-halo-Phe, D-Me5Phe, D-TMP, D-BIA and D-TBA; and E is selected from the group consisting of GlyNH₂ and AzaGlyNHR.

A more preferred set of embodiments is that wherein:

A is selected from the group consisting of L-(pyro)-Glu, D-(pyro)Glu, NAc-D-Phe and NAc-L-Pro;

B is selected from the group consisting of D-Phe, D-p-Cl-Phe, and DPG, as above;

C is selected from the group consisting of L-Trp and D-Trp, D-Nal (1), and D-Nal(2);

X is selected from the group consisting of D-Nal (2) D-TMP, D-BIA, and D-TBA; and E is selected from the group consisting of GlyNH₂ and AzaGlyNHR as above.

A still more preferred set of embodiments is that wherein

A is selected from the group consisting of L-(pyro)-Glu, D-(pyro)Glu, NAc-D-Phe, and NAc-L-Pro, as above;

B is selected from the group consisting of D-Phe, D-p-Cl-Phe, and DPG, as above;

C is selected from the group consisting of L-Trp and D-Trp, D-Nal(1) and D-Nal(2) as above;

X is D-Nal(2); and

E is selected from the group consisting of GlyNH₂ and AzaGlyNHR as above.

Those embodiments most particularly preferred are:
(pyro)Glu-DPG-Trip-Ser-Tyr-D-Nal(2)-Leu-Arg-Pro-GlyNH₂, abbreviated (DPG², D-Nal(2)⁶) LHRH;
(pyro)Glu-D-Phe-D-Trp-Ser-Tyr-D-Nal(2)-Leu-Arg-Pro-GlyNH₂ abbreviated (D-Phe², D-Trp³, D-Nal(2)⁶) LHRH;
(pyro)Glu-D-Phe-D-Nal(2)-Ser-Tyr-D-Nal(2)-Leu-Arg-Pro-GlyNH² abbreviated (D-Phe², D-Nal(2)³, D-Nal(2)⁶)LHRH;
NAc-L-Pro-D-Phe-D-Trp-Ser-Tyr-D-Nal(2)-Leu-Arg-Pro-GlyNH₂ abbreviated (NAc-L-Pro¹, D-Phe², D-Trp³,D-Nal(2)⁶)LHRH; and
NAc-D-Phe-D-p-Cl-Phe-D-Trp-Ser-Tyr-D-Nal(2)-Leu-Arg-Pro-GlyNH₂ abbreviated (NAc-D-Phe¹, D-p-Cl-Phe², D-Trp³, D-Nal(2)⁶)LHRH;
and also the corresponding peptides wherein the glycinamide at position 10 is replaced by AzaGlyNH₂.

In all of the above embodiments, the compound may also be prepared as the corresponding pharmaceutically acceptable salt. In all of the embodiments wherein NAc appears, the N-acetyl moiety is a prefered embodiment thereof.

Assay Procedures

The compounds of this invention and, particularly, the salts thereof, exhibit surprisingly potent and long lasting LHRH antagonist activity.

Primary measures of potency are ability to inhibit ovulation in rats, as assayed by the procedure of Corbin, A. and Beattie, C. W., *Endocrine Res. Commun.*, 2:1 (1975) and ability to inhibit LH release and ovulation in the rabbit, as per Phelps, C. P., et al, *Endocrinology* 100: 1526 (1977).

Other bioassays which are used for LHRH antagonists and for the compounds of the present invention are:

(a) inhibition of LHRH inducted FSH and LH release in the rat, in vivo; Vilchez-Martinez, J. A., et al, *Endocrinology*, 96: 1130 (1975); and, (b) inhibition of LH and FSH release by dispersed anterior pituitary cell cultures as measured by radioimmuno assay. (Vale, W., et al, *Endocrinology* 91: 562 (1972).

Antagonist Effects and Utilities

The following utilities flow from the antagonist effect of the compounds herein:
female contraception;
ovulation suppression or delay;
induction of parturition;
synchronization of ovulation;
estrus suppression;
growth promotion in female animals;
luteolysis, menses induction;
early, first trimester abortifacient;
therapy for endometriosis;
therapy for mammary cysts
therapy for polycystic ovary syndrome (Stein-Leventhal);
therapy for benign prostatic hypertrophy;
male contraception;
therapy for diseases which result from excessive gonadal hormone production in either sex;
functional castration in male food producing animals;
suppression of proestrous bloody discharge in dogs;
suppression of menopausal symptoms.

The aspect of the present invention which relates to particular uses for the above-described compounds is concerned with these utilities, most particularly; inhibition of ovulation and treatment of endometriosis in the female, and inhibition of spermatogenesis and treatment of prostatic hypertrophy in the male.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually) transdermally or intranasally. The most suitable route in any given case will depend upon the use, particular active ingredient, the subject involved, and the judgment of the medical practitioner. The compound or composition may also be administered by means of slow-release, depot or implant formulations as described more fully hereinbelow.

In general for the uses hereinabove described, it is expedient to administer the active ingredient in amounts between about 0.01 and 10 mg/kg body weight per day, preferably between about 0.1 and 1.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in *Remington's Pharmaceutical Sciences*, Mack Publishing Company, Easton, PA.,1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal adminstration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, *Sustained and Controlled Release Drug Delivery Systems*, J. R. Robinson ed., Marcel Dekker, Inc., New York, 1978. Particular reference with respect to LHRH type compounds may be found, for example, in U.S. Pat. No. 4,010,125.

Synthesis of the Peptides

The polypeptides of the present invention may be synthesized by any techniques that are known to those skilled in the peptide art. An excellent summary of the many techniques so available may be found in J. M. Stewart and J. D. Young, *Solid Phase Peptide Synthesis*, W. H. Freeman Co., San Francisco, 1969, and J. Meienhofer, *Hormonal Proteins and Peptides*, Vol. 2, p. 46. Academic Press (New York), 1973 for solid phase peptide synthesis and E. Shcroder and K. Lubke, *The Peptides*, Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Preferred Embodiments of Synthesis

A particularly preferred method of preparing compounds of the present invention involves solid phase peptide synthesis.

In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; for tyrosine:benzyl, o-bromobenzyloxycarbonyl, 2,6-dichlorobenzyl, isopropyl, cyclohexyl, cyclopentyl and acetyl; for serine:benzyl and tetrahydropyranyl; for histidine:benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be glycinamide, a particularly useful support is the benzhydrylaminopolystyrene-divinylbenzene polymer described by P. Rivaille, et al, *Helv. Chim. Acta.*, 54, 2772 (1971). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichlormethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroxyimides or oximes. Alternately, protected amino acid active esters (e.g. p-nitrophenyl, pentaflorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by tranesterification, e.g., with methanol, followed by aminolysis. The protected peptide may be purified at this point by silica gel chromatography. The removal of the side chain protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. For the glycine terminal peptides on the benzyhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing.

If a racemic amino acid is used in the 1, 2, 3 or 6 position, the diastereomeric nonapeptide or decapeptide final products are separated, and the desired peptide containing a D-amino acid in the appropriate position is isolated and purified, preferably during the above-described chromatographic process.

The preparation of peptides having C-terminal azaglycine amides is preferably done using classical peptide solution synthesis using known peptide intermediates. This is described in more detail in Example 3.

Thus, in another aspect the present invention relates to a method for preparing compounds of the invention and of the pharmaceutically acceptable salts thereof which process comprises:
  removing protecting groups and, optionally, covalently bound solid support from a protected polypeptide to afford a compound of Formula (I) or a salt thereof, and optionally
    (a) converting a compound of Formula (I) to a pharmaceutically acceptable salt, or
    (b) converting a salt of a compound of Formula (I) to a pharmaceutically acceptable salt, or
    (c) decomposing a salt of a compound of Formula (I) to a free polypeptide of Formula (I).

The following examples are given to enable those skilled in the art to more fully understand and practice the present invention. They should not be construed as a limitation upon the scope of the invention, but merely as being illustrative and representative thereof.

Preparation A

To an oven dried flask containing 0.1 L. of absolute ethanol (distilled from magnesium ethoxide) was added 1.52 g. of sodium metal. When hydrogen evolution ceased, 10.21 g. of ethyl 2-acetamido-2-cyanoacetate and 13.26 g. of 2-bromomethylnaphthalene were added to the solution. The solution was heated at reflux for 1 hour and then cooled. The ethanol was removed under reduced pressure and the residue was taken up in ethyl acetate. The organic layer was washed with two 50 mL. portions of water, one 50 mL. portion of saturated sodium chloride solution, and was dried over magnesium sulfate. The solution was filtered, the solvent was stripped off at reduced pressure and the residue was hydrolyzed in 100 mL. of concentrated hydrochloric acid at reflux for 2 hours.

The hydrolysis mixture was cooled and the precipitate of crude product was filtered. The crude product was redissolved in 0.5 L. of hot water containing 5 mL. of concentrated hydrochloric acid treated with charcoal, and the pH of the solution was adjusted to 6 with concentrated ammonium hydroxide. The precipitate was filtered and dried in vacuo to yield 11.3 g. of pure 3-(2-naphthyl)-D,L-alanine of melting point 230°–232° C.

Repeating the above procedure, substituting a stoichiometrically equivalent amount of
  1-bromomethylnaphthalene,
  9-bromomethylanthracene,
  9-bromomethylfluorene,
  2-bromomethylfluorene,
  2-bromomethylanthracene,
  1-bromomethylanthracene,
  α-chloroisodurene,
  4-bromomethylbiphenyl,
  1-bromomethyladamantane,
  3-bromomethylphenanthrene
  1-chloromethyl-2,4,6tri-(n-butyl)benzene, and
  1-chloromethyl-2,3,4,5,6-pentamethylbenzene,
for 2-bromomethylnaphthalene there are obtained the following amino acids:
  3-(1-naphthyl)-D,L-alanine, m.p. 185°–187° C.,
  3-(9-anthryl)-D,L-alanine, m.p. 290° C. (HCl salt),
  3-(9-fluorenyl)-D,L-alanine,
  3-(2-fluorenyl)-D,L-alanine, m.p. 264°–269° C.,
  3-(2-anthryl)-D,L-alanine,
  3-(1-anthryl)-D,L-alanine,
  3-(2,4,6-trimethylphenyl)-D,L-alanine, m.p. 235°–237° C.,
  3-(4-biphenylyl)-D,L-alanine, m.p. 290° C.,
  3-(1-adamantyl)-D,L-alanine,
  3-(3-phenanthryl)-D,L-alanine,
  3-(2,4,6-tri(n-butyl)phenyl)-D,L-alanine and
  3-(2,3,4,5,6-pentamethylphenyl)-D,L-alanine, respectively.

Preparation B

A solution of 18.2 g. 1,1-diphenylethylene, 25.3 g. methyl α-methoxy-N-benzyloxycarbonylglycinate, and 1.5 g. 2-naphthalenesulfonic acid in 300 mL. dry benzene was refluxed for 2 days. The crude product was purified on a column of silicic acid using a gradient of CH$_2$Cl$_2$ to CH$_2$Cl$_2$/EtOAc (18:1). The purified methyl 2-[1-(2,2-diphenylethylenyl)]-N-benzyloxycarbonylglcyinate was hydrolyzed to the corresponding acid with a solution of 10.9 g KOH in 350 mL. of 10% aqueous methanol. The resultant crude acid was dissolved in 100 mL. of 95% ethanol containing 3 mL. of conc. HCl and hydrogenated in the presence of 2 g. of 10% Pd on carbon for 24 hours to yield 2.4 g. of 3-(2,2-diphenylmethyl)-D,L-alanine, m.p. 235°–237° C.

Preparation C

To a solution of 12.9 g. of 3-(2-naphthyl)-D,L-alanine in 120 mL. of 1 M NaOH was added 6.23 mL. of acetic anhydride and 60 mL of 1 M NaOH during ½ hour at 0° C. The pH was adjusted to 2 with conc. HCl and the resultant precipitate was filtered. The solid was recrystallized from 60% aqueous ethanol to yield 12.2 g. of N-acetyl-3-(2-naphthyl)-D,L-alanine.

To a solution of 15 g. of this N-acetyl amino acid in 240 ml. of dry methanol was added 15.8 mL. of boron trifluoride etherate and the mixture was refluxed for 1 hour. The alcohol was evaporated, 200 mL. water was added and the solution was extracted with ethyl acetate. The organic layer was washed with aqueous base and acid, dried over MgSO$_4$, filtered, and stripped to an oil. Crystallization of this oil from ethyl acetate/hexane gave 14.2 g. of methyl N-acetyl-3-(2-naphthyl)-D,L-alaninate, m.p. 79°–80° C.

Repeating the above procedure, substituting a stoichiometrically equivalent amount of 3(1-naphthyl)-D,L-alanine,
3(2-fluorenyl)-D,L-alanine,
3(2-anthryl)-D,L-alanine,
3(1-anthryl)-D,L-alanine, and
3-(2,2-diphenylmethyl)-D,L-alanine for 3-(2-naphthyl)-D,L-alanine there are obtained methyl N-acetyl-3-(1-naphthyl)-D,L-alaninate, m.p. 97.5°–98° C.,
methyl N-acetyl-3-(2-fluorenyl)-D,L-alaninate, m.p. 170°–171° C.,
methyl N-acetyl-3-(2-anthryl)-D,L-alaninate, and
methyl N-acetyl-3-(2,2-diphenylmethyl)-D,L-alaninate, m.p. 113°–114° C., respectively.

Preparation D

A solution of 6.6 g. of methyl N-acetyl-3-(2-naphthyl)-D,L alaninate in a mixture of 300 mL. of dimethylsulfoxide, 120 mL. of 1 M KCl and 780 mL. of H$_2$O was treated with 33.6 mg of the enzyme subtilisin in 3 mL. of 0.1 M KCl. The pH was maintained at 7 by means of automatic titration with 0.2 M NaOH by a Radiometer pH stat. After 30 minutes 70 mL. of NaOH solution had been taken up and the hydrolysis was stopped. The solution was made basic with 12 g. NaHCO$_3$ and was extracted with ethyl acetate. The organic layer contained methyl N-acetyl-3-(2-naphthyl)-D-alaninate. Crystalization from ethyl acetate/hexane gave a yellow solid, m.p. 80°–81° C.

This was converted to the free amino acid and then to the N-Boc amino acid as follows:

A solution of 2.5 g of methyl N-acetyl-3-(2-naphthyl)-D-alaninate in 60 ml of 6N HCl was heated at 120°–130° for 3 hours and cooled to room temperature. The white precipitate which formed was collected and recrystallized from 50 ml of H$_2$O containing 1 ml of 12N HCl by neutralization with NH$_4$OH to pH 6, and dried in vacuo to yield 1.2 g of 3-(2-naphthyl)-D-alanine, m.p. 242°–244°, $[\alpha]_D^{25}$ 26.6° (c 0.5, CH$_3$CO$_2$H).

A stirred solution of 3-(2-naphthyl)-D-alanine in a mixture of 55 ml of 1N NaOH, 10 ml H$_2$O, and 20 ml dioxane was treated with 1.48 g of di-tert-butyl dicarbonate and 0.22 g of magnesium oxide at 0°. After 1.5 hours an additional 0.3 g of di-tert-butyl dicarbonate was added and the mixture was allowed to come to room temperature. The solid was removed by filtration and the filtrate was concentrated to 50 ml. This aqueous solution was brought to pH 2.5 with NaHSO$_4$ and extracted with ethyl acetate. The organic layer was washed with 5% NaHSO$_4$, water and saturated salt solution. The ethyl acetate solution was dried over magnesium sulfate, filtered and concentrated to an oil which was crystallized from ether/hexane to yield 1.3 g of N-Boc 3-(2-naphthyl)-D-alanine, m.p. 90°–91°, $[\alpha]_D^{25}$ −32.6° (c 0.8, MeOH).

Repeating the above procedure substituting a stoichiometrically equivalent amount of methyl N-acetyl-3-(1-naphthyl)-D,L-alaninate,
methyl N-acetyl-3-(2-fluorenyl)-D,L-alaninate,
methyl N-acetyl-3-(2-anthryl)-D,L-alaninate, and
methyl N-acetyl-3-(2,2-diphenylmethyl)-D,L-alaninate for methyl N-acetyl-3-(2-naphthyl)-D,L-alaninate there are obtained the following N$^\alpha$-Boc amino acids, via the corresponding free amino acids:

N-Boc-3-(1-naphthyl)-D-alanine, m.p. 92°–93° C., $[\alpha]_D^{25}$ 54.8° (c 0.5 MeOH),
N-Boc-3-(2-fluorenyl)-D-alanine, m.p. 161°–163° C. (dec.),
N-Boc-3-(2-anthryl)-D-alanine, and
N-Boc-3-(2,2-diphenylmethyl)-D-alanine, m.p. 153°–154° C., respectively.

Preparation E

In a Parr hydrogenation bottle was placed 0.85 g. of 3-(2-naphthyl)-D-alanine, 100 ml. of 2 M hydrochloric acid, and 0.85 g. of Adam's catalyst (PtO$_2$). The solution was packed under 60 lb/in$^2$ of H$_2$ gas for 20 hours in a Parr hydrogenation apparatus. The mixture was heated to dissolve the white precipitate and was filtered through diatomaceous earth. Concentration of the solution at reduced pressure followed by lyophilization from water yielded 0.8 g. of 3-(2-perhydronaphthyl)-D-alanine as a white solid of mp 230°–232° C.

This material was dissolved in a mixture of 3.2 ml. 1N-NaOH, 5 ml. water, and 15 ml. dioxane, and was treated with 0.14 g MgO and 0.85 g. di-tert-butyldicarbonate. After 1 hour at 0° C. and 2 hours at 25° C. the suspension was filtered, concentrated to dryness at reduced pressure, the residue dissolved in water, washed with diethyl ether, and acidified to pH 2 with NaHSO$_4$. The acidified aqueous layer was extracted three times with ethyl acetate and the extracts were combined, dried over MgSO$_4$, filtered, and concentrated to give 0.75 g. of N-Boc-3-(2-perhydronaphthyl)-D-alanine as white oil.

A 0.1 g. portion of this material was dissolved in 5 ml tetrahydrofuran and titrated at 0° C. with freshly prepared diazomethane until the bright yellow color persisted. The reaction was quenched with 1 ml acetic acid, the solvent was evaporated and the residue was partitioned between 75 ml. ethyl acetate and 75 ml. water. The organic layer was washed with 5% NaHCO$_3$, water, 5% NaHSO$_4$, water, saturated NaCl solution, and dried over MgSO$_4$. The solution was filtered, concentrated under reduced pressure, and loaded on a preparative thin layer chromatography plate (750$\mu$ thick, silica gel, 20×20 cm.) The plate was developed with dichloromethane/ethyl acetate (18/1) and the product band was removed. The silica gel from the product band was washed with dichloromethane/ethyl acetate (9:1) on a fritted glass funnel and the filtrate was concentrated to give 0.1 g. of methyl N-Boc-3-(2-perhydronaphthyl)-D-alaninate as a light yellow oil.

This material was obtained as a mixture of two isomers at the 2 position of the perhydronaphthalene nucleus. These diastereomeric compounds may be separated on a high performance liquid chromatography column (Lichrosorb silica gel 60, 5 micron) with ethyl acetate/hexane (1:9) as eluent and hydrolyzed to the free acid, N-Boc-3-(2-perhydronaphthyl)-D-alanine.

Repeating the above procedure substituting a stoichiometrically equivalent amount of
3-(1-naphthyl)-D-alanine,
3-(2,2-diphenylmethyl)-D-alanine,
3-(2,4,6-trimethylphenyl)-D,L-alanine,
3-(4-biphenylyl)-D,L-alanine,
3-(2,4,6-tri(n-butyl)phenyl)-D,L-alanine, and
3-(2,3,4,5,6-pentamethylphenyl)-D,L-alanine,
for 3-(2-naphthyl)-D-alanine there are obtained the following N-Boc amino acids:
N-Boc-3-(1-perhydronaphthyl)-D-alanine,
N-Boc-3-(perhydro-2,2-diphenylmetyl)-D-alanine,
N-Boc-3-(2,4,6-trimethylcyclohexyl)-D,L-alanine,
N-Boc-3-(perhydro-4-biphenylyl)-D,L-alanine,
N-Boc-3-(2,4,6-tri(n-butyl)cyclohexyl)-D,L-alanine, and
N-Boc-3-(2,3,4,5,6-pentamethylcyclohexyl)-D,L-alanine, respectively.

Preparation F 4.9 g of Boc-glycine was dissolved in a mixture of 50 ml. ethanol and 50 ml. distilled water. The pH of the solution was brought to 7 with aqueous cesium bicarbonate. The solvent was then removed under vacuum.

After 18 hours of drying under high vacuum, the residue was dissolved in 150 ml. dry DMF. 25 g chloromethylated polystyrene—1% divinylbenzene (Merrifield) resin (corresponding to 25 mmole chloride) was added. The mixture was shaken at 50° for 24 hours, filtered, and the resin was then washed sequentially with DMF, water, and ethanol. The resin was dried under vacuum for 3 days to yield 28.34 g of Boc-Gly-O-Resin.

EXAMPLE 1

In the reaction vessel of a Beckman 990 Peptide Synthesizer was placed 7.29 g. (0.8 mmol.) of Boc-Glu-O-Resin (Lab Systems, Inc.). Amino acids were added sequentially to this resin by means of a synthesis program, as follows:

| Step | | | | |
|---|---|---|---|---|
| 1 | $CH_2Cl_2$ wash | | 1 time | 1.5 min |
| 2 | 50% $CF_3CO_2H/CH_2Cl_2$ - deprotection | | 1 time | 1.5 min |
| 3 | 50% $CF_3CO_2H/CH_2Cl_2$ - deprotection | | 1 time | 30 min |
| 4 | $CH_2Cl_2$ wash | | 3 times | 1.5 min |
| 5 | 10% triethylamine/$CH_2Cl_2$ | | 2 times | 1.5 min |
| 6 | $CH_2Cl_2$ wash | | 3 times | 1.5 min. |
| 7 | $N^\alpha$—Boc-amino acid solution | | 1 time | add |
| 8 | N,N'—dicyclohexylcarbodiimide solution | | 1 time | add |
| 9 | $CH_2Cl_2$ rinse and hold - coupling | | 1 time | coupling reaction 2 hr |
| 10 | $CH_2Cl_2$ - rinse add | | 1 time | 1.5 min |
| 11 | $CH_2Cl_2$ wash | | 3 times | 1.5 min |
| 12 | ethanol wash | | 3 times | 1.5 min |
| 13 | $CH_2Cl_2$ wash | | 3 times | 1.5 min |

Steps 1-13 complete a coupling cycle for one amino acid and completeness of the reaction is checked by the ninhydrin method of E. Kaiser, et al., *Anal. Biochem.*, 34, 595 (1970).

The resin was coupled sequentially with a 2.5 molar excess of each protected amino acid and DCC. Thus, the resin was treated during successive coupling cycles with
3.01 g. Boc-Pro-OH,
5.99 g. Boc-Arg(Tosyl)-OH,
3.49 g. Boc-Leu-OH. $H_2O$ At this point, the resulting tetra peptide resin was divided into smaller batches. A 1.08 g. batch was carried forward by further coupling in successive cycles with
0.315 g. Boc-D-Nal(2)-OH,
0.44 g. Boc-Tyr(2,6-dichlorobenzyl)-OH,
0.295 g. Boc-Ser(Benzyl)-OH,
0.304 g. Boc-Trp-OH,
0.265 g. Boc-D-Phe-OH
0.129 g. pyroglutamic acid.

The resin was removed from the reaction vessel, washed with $CH_2Cl_2$, and dried in vacuo to yield 1.66 g. of protected polypeptide resin. The protected peptide was removed from the resin by treatment at room temperature for 24 hours with 50 ml. of methenol saturated at 0° with ammonia. The resin beads were filtered and washed sequentially with methanol and DMF. Solvent was removed from the filtrate under vacuum to yield the protected peptide as 0.9 g. of yellow oil.

The protecting groups were removed by treatment with 10 ml. anhydrous liquid HF in the presence of 1 ml. of anisole (scavenger) in a Kel-F reaction vessel at 0° C. for 30 minutes. The HF was evaporated under vacuum and the residue of (pyro)-Glu-D-Phe-Trp-Ser-Tyr-D-Nal(2)-Leu-Arg-Pro-GlyNH2, as its HF salt, was washed with ether. The residue was then extracted with glacial acetic acid. The acetic acid extract with lyophilized to yield 0.5 g. of crude material.

The crude material was converted to the acetate salt by passage in water through a column of AG3X (a weakly basic tertiary amine resin) which had been converted to the acetate form. Lyophilization of the eluate yielded 0.5 g. of the crude peptide acetate salt as a white solid.

The crude peptide was purified by high performance liquid chromatography on a 0.8×50 cm. column of Licroprep Rp-18 (25–40 micron) equilibrated to the running buffer 35% $CH_3CN/65\%H_2O$ (0.03 M in $NH_4OAc$, pH.5). The major UVabsorbing (280 nm) peak eluting at approximately 6 column volumes was collected, concentrated to dryness, and lyophilized 3 times from distilled water to yeild 75 mg of pure (pyro)-Glu-D-Phe-Trp-Ser-Tyr-D-Nal(2)-Leu-Arg-Pro-GlyNH2; $[\alpha]_D^{25} = -38.6$ (C 0.5HOAc); mp: 162°–165°.

EXAMPLE 2

For the synthesis of analogues with a C-terminal Pro-NHCH2CH3, a synthesis program identical to that described in Example 1 was used. The Beckman 990 Synthesizer reaction vessel was loaded with 2.13 g. of Boc-Pro-O-Resin, prepared by the reaction of equimolar ratios of the dry cesium salt of Boc-Pro-OH with chloromethyl-polystyrene/1% divinylbenzene (Lab Systems, Inc.). The quantity of Boc-Pro-O-Resin taken contained 1.4 mmol. of proline.

The resin was coupled sequentially with a 2.5 molar excess of each protected amino acid and DCC. Thus, the resin was reacted during successive coupling cycles with 1.61 g. Boc-Arg(Tosyl)-OH,
0.93 g. Boc-Leu-Oh H$_2$O,
0.94 g. Boc-3-(2-naphthyl)-D-alanine and 0.49 g. of 1-hydroxybenzotriazole,
1.75 g. N-Boc-O-2-bromobenzyloxycarbonyl-L-tyrosine, and 1.11 g. Boc-Ser(Bensyl)-OH.

At this point in the synthesis the quantity of protected polypeptide resin was split in half and one half was carried through to completion by sequential reaction with 0.57 g. Boc-Trp-OH,
0.480 g. Boc-D-Phe-OH
0.21 g. pyroglutamic acid.

The resin was removed from the reaction vessel, washed with CH$_2$Cl$_2$, and dried in vacuo to yield 2.26 g. of protected polypeptide resin.

The protected polypeptide was cleaved from the resin by aminolysis with 25 mL. of ethylamine for 18 hours at 2° C. The ethylamine was allowed to evaporate and the resin was extracted with methanol. The methanol was evaporated to yield 1.39 g. of (pyro)Glu-D-Phe-Trp-Ser(Benzyl)-Tyr(2-bromobenzyloxycarbonyl)-D-Nal(2)-Leu-Arg(Tosyl)-Pro-NHCH$_2$CH$_3$ with a mixture of 3 mL. anisole and 30 mL. redistilled (from CoF$_3$) anhydrous liquid HF at 0° C. for 30 minutes in a Kel-F reaction vessel. The HF was evaporated under vacuum and the residue was washed with ether. The residue was dissolved in 2 M acetic acid and lyophilized to yield 0.82 g. of crude (pyro)Glu-D-Phe-Trp-Ser-Tyr-Leu-Arg-Pro-NHCH$_2$CH$_3$ as its acetic acid addition salt. Final purification was achieved by preparative high permformance liquid chromatography of a 20 mg. sample on a 0.9×550 mm. column of 40–50μ. octadecylsilylated silica (Merck, Lichroprep C$_{18}$). The eluant was 64% 0.03 M NH$_4$OAc/36% acetonitrile. In four runs a total of 61 mg. of crude material was purified. After three lyophilizations from water, 15 mg. of pure pyroglutamyl-D-phenylalanyl-tryptophyl-seryl-tyrosyl-3-(2-naphthyl)-D-alanyl-leucyl-arginyl-proline ethylamide was obtained as its acetic acid addition salt.

Repeating the above cleavage, substituting a stoichiometric amount of:
n-butylamine,
cyclopropylamine,
cyclohexylamine,
trifluoromethylamine,
pentafluoroethylamine, and
2,2,2-trifluoroethylamine
for ethylamine there are obtained the corresponding
n-butylamide,
cyclopropylamide,
cyclohexylamide,
trifluoromethylamide,
pentafluoroethylamide, and
2,2,2-trifluoroethylamide
of the aforementioned nonapeptide.

EXAMPLE 3

Compounds of Formula I wherein E is

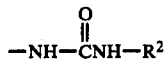

may be prepared by classical solution synthesis.

For example, the following approach may be used wherein "AzaGlyNHR$_2$" is

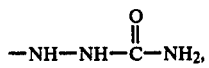

to prepare the peptide as the free peptide or salt.

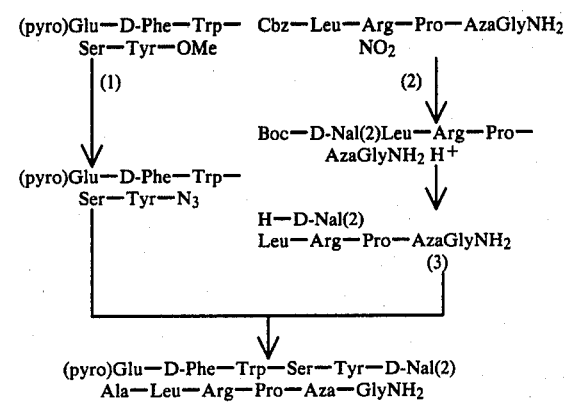

The coupling of the individual fragments may proceed by the acyl axide methyl (J. Honzel, et al, *Col. Czech. Chem. Comm,* 26, 2333 (1971), by DCC/HBT coupling or other racemization free fragment coupling techniques. Compound (2) is known: A. S. Dutta, et al., *J. Chem. Soc. Perkin I,* 1979, 379, and compound (1) may be prepared by methods analogous to those in Example 1. Compound (3) is prepared from (2) by removal of the Cbz and nitro groups by hydrogenolysis, followed by coupling with N-Boc-3-(2-naphthyl)-D-alanine using DCC/HBT or other coupling agent known in the art. See Dutta, et al, supra, for a similar LHRH analogue synthesis.

Similarly, utilizing other amino acids in place of those used to prepare (1) and (2) the following may be prepared: (NAc in the list below is the acetamide.)
(D-Phe$^2$, D-Nal(2)$^3$, D-Nal(2)$^6$, AzaGlyNH$_2$$^{10}$)LHRH;
(D-Phe$^2$, D-Trp$^3$, D-Nal(2)$^6$, AzaGlyNH$_2$$^{10}$)LHRH;
(D-Phe$^2$, D-Trp$^3$, D-BIA$^6$, AzaGlyNH$_2$$^{10}$)LHRH;
(NAc-D-Phe$^1$, D-p-Cl-Phe$^2$, D-Trp$^3$, D-Nal(2)$^6$ AzaGlyNH$_2$$^{10}$)LHRH;
NAc-L-Pro$^1$, DPG$^2$, D-Trp$^3$, D-Nal(2)$^6$, AzaGlyNH$_2$$^{10}$) LHRH;
(NAc-D-Phe$^1$, D-Phe$^2$, D-Trp$^3$, D-BIA$^6$, AzaGlyNH$_2$$^{10}$)LHRH;
(NAc-D-Phe$^1$, D-p-Cl-Phe$^2$, D-Trp$^3$, D-TBA$^6$, AzaGlyNH$_2$$^{10}$)LHRH;
(NAc-L-Pro$^1$, D-Phe$^2$, D-Trp$^3$, D-TMP$^6$, AzaGlyNH$_2$$^{10}$)LHRH;
(D-(pyro)Glu$^1$, D-Phe$^2$, D-Trp$^3$, D-Nal(2)$^6$, AzaGlyNH$_2$$^{10}$)LHRH;
(DPG$^2$, D-Nal(2)$^6$, AzaGlyNH$_2$$^{10}$)LHRH;
(NAc-L-Pro$^1$, D-Phe$^2$, D-Trp$^3$, D-Nal(2)$^6$, AzaGlyNH$_2$$^{10}$)LHRH;
(D-Phe$^2$, D-Trp$^3$, D-Nal(2)$^6$, AzaGlyNH$_2$$^{10}$)LHRH.

EXAMPLE 4

Repeating the procedure of Example 1 and utilizing either a D-amino acid or a D,L amino acid at positions at which amino acid replacements from LHRH occur (in the latter case, separating the diastereomeric peptides during chromatography), substituting the appropriate amino acids in the solid phase synthesis sequence, there may be obtained the following decapeptides which are isolated and characterized as their acetic acid addition salts: (NAc in the list below is the acetimide.)

(D-Phe$^2$, D-Nal(2)$^3$, D-Nal(2)$^6$)LHRH; $[\alpha]_D^{25} = -28.2$ (C 0.4HOAc), m.p. = 162°–164°;
(D-Phe$^2$, D-trp$^3$, D-Nal(2)$^6$)LHRH; $[\alpha]_D^{25} = -27.5$ (C 0.5 HOAc), m.p. 172°–174°;
(D-Phe$^2$, D-Trp$^3$, D-BIA$^6$)LHRH;
(NAc-D-Phe$^1$, D-p-Cl-Phe$^2$, D-Trp$^3$, D-Nal(2)$^6$)LHRH;
(NAc-L-Pro$^1$, DPG$^2$, D-Trp$^3$, D-Nal(2))LHRH;
(NAc-D-Phe$^1$, D-Phe$^2$, D-Trp$^3$, D-BIA$^6$)LHRH;
(NAc-d-Phe$^1$, D-p-Cl-Phe$^2$, D-Trp$^3$, D-TBA$^6$)LHRH;
(NAc-L-Pro$^1$, D-Phe$^2$, D-Trp$^3$, D-TMP$^6$)LHRH;
(D-(pyro)Glu$^1$, D-Phe$^2$, D-Trp$^3$, D-Nal(2)$^6$)LHRH;
(DPG$^2$, D-Nal(2)$^6$)LHRH;
(NAc-L-Pro$^1$, D-Phe$^2$, D-Trp$^3$, D-Nal(2)$^6$)LHRH; $[\alpha]_D^{25} = -34.36$ (C 0.2 HOAc) m.p. = 176°–178°.

EXAMPLE 5

Repeating the procedure of Example 2 and utilizing either a D-amino acid or a D,L amino acid at position at which amino acids different from those in LHRH occur, (in the latter case, separating the diastereomeric peptides during chromatography), substituting the appropriate amino acids in the solid phase synthesis sequence, there may be obtained the following nonapeptides with are isolated and characterized as their acetic acid addition salts: (NAc in the list below is the acetamide.)

(pyro)Glu-D-pCl-Phe-Trp-Ser-Tyr-D-Nal(2)-Leu-Arg-Pro as its ethylamide, n-butylamide, cyclopropylamide, cyclohexylamide, trifluoromethylamide, pentafluroethylamide and 2,2,2-trifluoroethylamide (pyro)Glu-D-Phe-Trp-Ser-Tyr-D-Nal(2)-Leu-Arg-Pro as its ethylamide, n-butylamide, cyclopropylamide, cyclohexylamide, trifluoromethylamide, pentafluoroethylamide and 2,2,2-trifluoroethylamide (pyro)Glu-D-DPG-Trp-Ser-Tyr-D-Nal(2)-Leu-Arg-Pro as its ethylamide, n-butylamide, cyclopropylamide, cyclohexylamide, trifluoromethylamide, pentafluoroethylamide and 2,2,2-trifluoroethylamide NAc-L-Pro-D-Phe-d-Trp-Ser-Tyr-D-Nal(2)-Leu-Arg-Pro as its ethylamide, n-butylamide, cyclopropylamide, cyclohexylamide, trifluoromethylamide, pentafluoroethylamide and 2,2,2-trifluoroethylamide NAc-D-Pro-DPG-Trp-Ser-Tyr-D-TBA-Leu-Arg-Pro as its ethylamide, n-butylamide, cyclopropylamide, cyclohexylamide, trifluoromethylamide, pentafluoroethylamide and 2,2,2-trifluoroethylamide (pyro)Glu-D-P-Cl-Phe-D-Phe-Ser-Tyr-D-TMP-Leu-Arg-Pro as its ethylamide, n-butylamide, cyclopropylamide, cyclohexylamide, trifluoromethylamide, pentafluoroethylamide and 2,2,2-trifluoroethylamide (pyro)Glu-d-Phe-D-Nal(2)-Ser-Tyr-D-BIA-Leu-Arg-Pro as its ethylamide, n-butylamide, cyclopropylamide, cyclohexylamide, trifluoromethylamide, pentafluoroethylamide and 2,2,2-trifluoroethylamide (pyro)Glu-D-Phe-Trp-Ser-Try-D-Nal(1)-Leu-Arg-Pro as its ethylamide, n-butylamide, cyclopropylamide, cyclohexylamide, trifluoromethylamide, pentafluoroethylamide and 2,2,2-trifluoroethylamide

EXAMPLE 6

A. A solution of 0.1 g. of the hydrogen fluoride salt of (pyro)Glu-D-Phe-Trp-Ser-Tyr-D-Nal(2) Leu-Arg-Pro-GlyNH$_2$ (See Example 1) is dissolved in 50 mL of water and passed through a column of 50 g Dowex 3 anion exchange resin which had previously been equilibrated with acetic acid and washed with deionized water. The column is eluted with deionized water and the effluent is lyophilized to yield the correspondung acetic acid salt of (pyro)Glu-D-Phe-Trp-Ser-Tyr-D-Nal(2)-Leu-Arg-Pro-Gly-NH$_2$, $[\alpha]_D^{25} - 38.6°$ (c 0.5,. HOAc) m.p. 162°–165°.

Repeating the above, substituting other acids for acetic acid during the equilibration of the resin, there may be obtained, for example, the corresponding salts with hydrochloric acid, hydrobromic acid, sulfuric acid, phosphroic acid, nitric acid, benzoic acid, and the like.

Similarly there may be prepared the acid addition salts of the other peptides analogous to LHRH, described herein.

B. In the case of salts of low water solubility, these may be prepaared by precipitation from water utilizing the desired acid. For example:

Zinc tannate salt - a solution of 10 mg of (pyro)Glu-D-Phe-Trp-Ser-Tyr-D-Nal(2)-Leu-Arg-Pro-Gly-NH$_2$ acetic acid salt in 0.1 mL of water was treated with a solution of 8 mg of tannic acid in 0.08 mL of 0.25 M NaOH. A solution of 5 mg of ZnSo$_4$ heptahydrate in 0.1 mL of water was immediately added to the solution of the LHRH analogue.

The resultant suspension was diluted with 1 mL water and the precipitate was centrifuged. The supernatnat was decanted and the residue was washed twice with 1 mL portions of water by centrifugation of the precipitate and decantation of the supernatant. The precipitate was dried in vacuo to yield 15 mg of the mixed zinc tannate salt of the above named LHRH analogue.

Pamoate salt—to a solution of 50 mg (pyro)Glu-D-Phe-Trp-Ser-Tyr-D-Nal(2)-Leu-Arg-Pro-Gly-NH$_2$ acetic acid salt in a mixture of 1.6 mL of ethanol and 0.1 mL of 0.25 M NaOh was added solution of 11 mg of pamoic acid in 0.3 mL of 0.25 M NaOH. The solvents were removed at reduced pressure and the residue was suspended in 2 mL of water, centrifuged, and the supernatant was decanted. The precipitate was washed with 1.5 mL H$_2$O, centrifuged, and the supernatant was decanted. The precipitate was dried in vacuo to yield 54 mg of the pamoate salt of the above named LHRH analogue.

In a similar manner other salts of low water solubility may be prepared.

C. Preparation of acid addition salt from free peptide

To a solution of 50 mg of (pyro)Glu-D-Phe-D-Trp-Ser-Tyr-D-Nal(2)-Leu-Arg-Pro-GlyNH$_2$ as the free base is added 30 mL of 1N acetic acid. The resulting solution is lyophilized to yield 50 mg. of the acetic acid salt of the above $\alpha_D^{25} - 27.5$ (c 0.5HOAc), mp: 172°–174°.

Similarly, replacing acetic acid with other acids (in stoichiometrically equivalent amounts relative to peptide) there was obtained other acid addition salts of the peptides herein, for example, the salts with hydrochloric acid, hydrobromic acid, sulfuric acid, phosphoric acid, nitric acid.

D. Preparation of salt with metal cation, e.g., zinc salt

To a solution of 50 mg (pyro)Glu-D-Phe-Trp-Ser-Tyr-D-Nal(2)-Leu-Arg-Pro-Gly-$NH_2$ acetic acid salt in a mixture of 0.4 mL of 0.25 M NaOH, 0.3 mL water, and 1 mL ethanol was added a solution of 15 mg of $ZnSO_4$ heptahydrate in 0.2 mL of water. The precipitate was centrifuged and the supernatant was decanted. The precipitate was washed with 1 mL of water by centrifugation and decantation of the supernatant. The precipitate was dried in vacuo to yield 48 mg of the zinc salt of the above named LH-RH analogue.

In a similar manner salts with other multivalent cations e.g. calcium, bismuth, barium, magnesium, aluminium, copper, cobalt, nickel, cadmium and the like, may be prepared.

EXAMPLE 7

A solution of 50 mg of (pyro)Glu-D-Phe-Trp-Ser-Tyr-D-Nal(2)-Leu-Arg-Pro-Gly-$NH_2$ acetic acid salt in 25 ml. of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid addition salts of compounds of the peptides herein, e.g., those mentioned in Example 6, may be converted to the corresponding free bases.

EXAMPLE 8

The following are typical pharmaceutical compositions containing, as active ingredient, an LHRH antagonist of the present invention, for example (pyro)Glu-D-Phe-Trp-Ser-Tyr-D-Nal(2)-Leu-Arg-Pro-Gly$NH_2$, by itself or as a pharmaceutically acceptable salt, e.g., the acetic acid addition salt, the zinc salt, the zinc tannate salt, etc.

A. Tablet Formulations for Buccal (e.g. Sublingual) Administration

| 1. | LHRH Antagonist | 10.0 mg |
|---|---|---|
|  | Compressible Sugar, USP | 86.0 mg |
|  | Calcium Stearate | 4.0 mg |
| 2. | LHRH Antagonist | 10.0 mg |
|  | Compressible Sugar, USP | 88.5 mg |
|  | Magnesium Stearate | 1.5 mg |
| 3. | LHRH Antagonist | 5.0 mg |
|  | Mannitol, USP | 83.5 mg |
|  | Magnesium Stearate, USP | 1.5 mg |
|  | Pregelatinized Starch, USP | 10.0 mg |
| 4. | LHRH Antagonist | 10.0 mg |
|  | Lactose, USP | 74.5 mg |
|  | Pregelatinized Starch, USP | 15.0 mg |
|  | Magnesium Stearate, USP | 1.5 mg |

Method of Manufacture a. LH-RH Antagonist is dissolved in water, a sufficient quantity to form a wet granulation when mixed with the sugar portion of the excipients. After complete mixing, the granulation dried in a tray or fluid-bed dryer. The dry granulation is then screened to break up any large aggregates and then mixed with the remaining components. The granulation is then compressed on a standard tabletting machine to the specific tablet weight.

b. In this manufacturing method, all formulations would include 0.01% gelatin, USP. The gelatin would be first dissolved in the aqueous granulation solvent followed by the LH-RH analog. The remaining steps are as in (a) above.

Formulation 4 could also be used as a tablet for oral administration.

B. Long Acting Intramuscular Injectable Formulation

| 1. Long Acting I.M. Injectable - Sesame Oil Gel | |
|---|---|
| LHRH Antagonist | 10.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LH-RH analogue is then added aseptically with trituration. Particularly preferred LH-RH analogues are salts of low solubility, e.g. zinc salts, zinc tannate salts, pamoate salts, and the like. These exhibit, exceptionally long duration of activity.

| 2. Long Acting I.M. Injectable - Biodegradable Polymer Microcapsules | |
|---|---|
| LHRH Antagonist | 1% |
| 25/75 glycolide/lactide copolymer (0.5 intrinsic viscosity) | 99% |

Microcapsules (0–150$\mu$) of above formulation suspended in:

| Dextrose | 5.0% |
|---|---|
| CMC, sodium | 0.5% |
| Benzyl alcohol | 0.9% |
| Tween 80 | 0.1% |
| Water, purified q.s. | 100.0% |

25 mg of microcapsules would be suspended in 1.0 ml of vehicle.

C. Aqueous Solution for Intramuscular Injection

| LHRH Antagonist | 500 mg |
|---|---|
| Gelatin, nonantigenic | 5 mg |
| Water for injection q.s. ad | 100 ml |

Dissolve gelatin and LHRH antagonist in water for injection, then sterile filter solution.

D. Formulation for Rectal Administration

| Suppository Vehicle for Rectal Administration | |
|---|---|
| LHRH Antagonist | 5.0 mg |
| Witepsol H15 | 20.0 gm |

The LHRH antagonist is combined with the molten Witepsol H15, mixed well and poured into 2 gm molds.

We claim:

1. A compound of the formula

A—B—C—Ser—Tyr—X—Leu—Arg—Pro—E    (I)

and the pharmaceutically acceptable salts thereof, wherein:

X is a D-alanyl residue wherein one hydrogen on C-3 is replaced by:
 (a) a carbocyclic aryl-containing radical selected from the group consisting of phenyl substituted with three or more straight chain lower alkyl groups, naphthyl, anthryl, fluorenyl, phenanthryl, biphenylyl and benzhydryl; or
 (b) a saturated carbocyclic radical selected from the group consisting of cyclohexyl sustituted with three or more straight chain lower alkyl groups, perhydronaphthyl, perhydrobiphenylyl, perhydro-2, 2-diphenylmethyl, and adamantyl; or
 (c) a heterocyclic aryl containing radical selected from the group consisting of radicals represented by the following structural formulas:

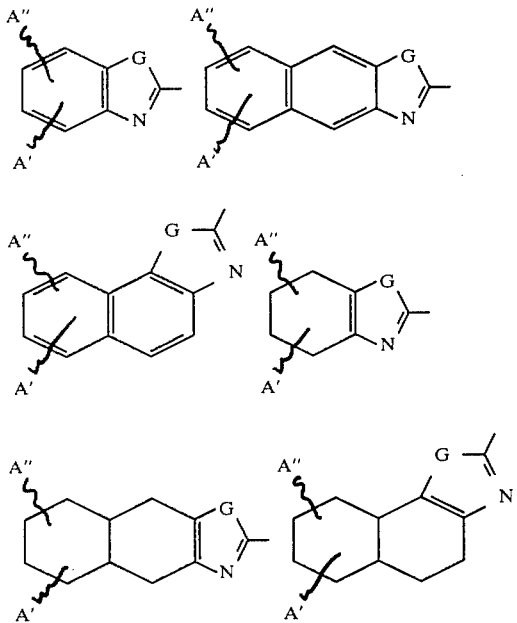

wherein A" and A' are independently selected from the group consisting of hydrogen, lower alkyl, chlorine, and bromine, and G is selected from the group consisting of oxygen, nitrogen, and sulfur;

A is an aminoacyl residue selected from the group consisting of L-pyroglutamyl, D-pyroglutamyl, N-acyl-L-prolyl, N-acyl-D-prolyl, N-acyl-D-tryptophanyl, N-acyl-D-phenylalanyl, N-acyl-D-p-halophenylalanyl, and N-acyl-X, wherein X is as defined previously;

B is a D-p-halophenylalanyl residue;

C is an amino acyl residue selected from the group consisting of L-tryptophanyl, D-tryptophanyl, D-phenylalanyl and X wherein X is as defined above;

E is glycinamide or —NH-R¹, wherein R¹ is lower alkyl, cycloalkyl, fluoro lower alkyl or

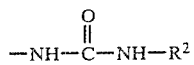

wherein R² is hydrogen or lower alkyl.

2. The compound of claim 1, and the pharmaceutically acceptable salts thereof, wherein
 A is selected from the group consisting of L-(pyro)-Glu, D-(pyro)Glu, NAc-D-Phe, NAc-D-Nal(1), NAc-D-Nal(2), NAc-D-p-halo-Phe, NAc-D-Me5-Phe, NAc-D-TMP, NAc-D-BIA, NAc-D-TBA, and NAc-L-Pro;
 B is D-p-F-Phe;
 C is selected from the group consisting of L-Trp, D-Trp, D-Phe, D-Nal(1), D-Nal(2), D-p-halo-Phe, D-Me5Phe, D-TMP, D-BIA and D-TBA;
 X is selected from the group consisting of D-Nal(1), D-Nal(2), D-p-halo-Phe, D-Me5Phe, D-TMP, D-BIA and D-TBA; and
 E is glycinamide or —NH-R, wherein R¹ is lower alkyl, cycloalkyl, fluoro lower alkyl or

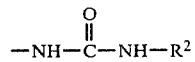

wherein R² is hydrogen or lower alkyl.

3. The compound of claim 2 and the pharmaceutically acceptable acid addition salts thereof, wherein:
 X is D-Nal(2).

4. The compound of claim 3 and the pharmaceutically acceptable acid addition salts thereof, wherein:
 A is NAc-Pro, C is D-Nal(2), and E is Gly-NH₂, i.e. NAc-Pro-D-p-F-Phe-D-Nal(2)-Ser-Tyr-D-Nal(2)-Leu-Arg-Pro-GlyNH₂.

5. The compound of claim 3 and the pharmaceutically acceptable acid addition salts thereof, wherein:
 A is NAc-Pro, C is D-Nal(2), and E is ProNHEt, i.e. NAc-Pro-D-p-F-Phe-D-Nal(2)-Ser-Tyr-D-Nal(2)-Leu-Arg-Pro-ProNHEt.

6. The compount of claim 3 and the pharmaceutically acceptable acid addition salts thereof, wherein:
 A is NAc-Pro, C is D-Nal(2) and E is AzaGlyNH₂, i.e. NAc-Pro-D-p-F-Phe-D-Nal(2)-Ser-Tyr-D-Nal(2)-Leu-Arg-Pro-AzaGlyNH₂.

7. The compound of claim 3 and the pharmaceutically acceptable acid addition salts thereof, wherein:
 A is NAc-D-Nal(2), C is D-Nal(2) and E is GlyNH₂, i.e. NAc-D-Nal(2)-D-p-F-Phe-D-Nal(2)-Ser-Tyr-D-Nal(2)-Leu-Arg-Pro-GlyNH₂.

8. The compound of claim 3 and the pharmaceutically acceptable acid addition salts thereof, wherein:
 A is NAc-D-Nal(2), C is D-Nal(2) and E is ProNHEt, i.e. NAc-D-Nal(2)-D-p-F-Phe-D-Nal(2)-Ser-Tyr-D-Nal(2)-Leu-Arg-Pro-ProNHEt.

9. The compound of claim 3 and the pharmaceutically acceptable acid addition salts thereof, wherein:
 A is NAc-D-Nal(2), C is D-Nal(2) and E is AzaGlyNH₂, i.e., NAc-D-Nal(2)-D-p-F-Phe-D-Nal(2)-Ser-Tyr-D-Nal(2)-Leu-Arg-Pro-AzaGlyNH₂.

10. The compound of claim 3 and the pharmaceutically acceptable acid addition salts thereof, wherein:
 A is NAc-Pro, C is L-Trp and E is GlyNH₂, i.e., NAc-Pro-D-p-F-Phe-L-Trp-Ser-Tyr-D-Nal(2)-Leu-Arg-Pro-GlyNH₂.

11. The compound of claim 3 and the pharmaceutically acceptable acid addition salts thereof, wherein:
 A is NAc- Pro, C is L-Trp and E is AzaGlyNH₂, i.e., NAc-Pro-D-p-F-Phe-L-Trp-Ser-Tyr-D-Nal(2)-Leu-Arg-Pro-AzaGlyNH₂.

12. The compound of claim 3 and the pharmaceutically acceptable acid addition salts thereof, wherein:

A is NAc-D-Nal(2), C is L-Trp and E is GlyNH$_2$, i.e., NAc-D-Nal(2)-D-p-F-Phe-L-Trp-Ser-Tyr-D-Nal(2)-Leu-Arg-Pro-GlyNH$_2$.

13. The compound of claim 3 and the pharmaceutically acceptable acid addition salts thereof, wherein:
A is NAc-D-Nal(2), C is L-Trp and E is AzaGlyNH$_2$, i.e., NAc-D-Nal(2)-D-p-F-Phe-L-Trp-Ser-Tyr-D-Nal(2)-Leu-Arg-Pro-AzaGlyNH.

14. The compound of claim 1 and the pharmaceutically acceptable salts thereof, wherein A is NAc-L-Pro, B is D-p-Cl-Phe, C is D-Trp, and E is AzaGlyNH$_2$, i.e., NAc-L-Pro-D-p-Cl-Phe-D-Trp-Ser-Tyr-D-Nal(2)-Leu-Arg-Pro-AzaGlyNH$_2$.

15. The compound of claim 1 and the pharmaceutically acceptable salts thereof, wherein A is NAc-L-Pro, B is D-p-Cl-Phe, C is D-Trp, and E is GlyNH$_2$, i.e., NAc-L-Pro-D-p-Cl-Phe-D-Trp-Ser-Tyr-D-Nal(2)-Leu-Arg-Pro-GlyNH$_2$.

16. The compound of claim 1 and the pharmaceutically acceptable addition salts thereof wherein A is NAc-L-Pro, B is D-p-Cl-Phe, C is D-Trp and E is PronNHEt, i.e., NAc-L-Pro-D-p-Cl-Phe-Pro-D-Trp-Ser-Tyr-D-Nal(2)-Leu-Arg-Pro-ProNHEt.

17. The compound of claim 1 and the pharmaceutically acceptable salts thereof, wherein A is NAc-L-Pro, B is D-p-Cl-Phe, C is D-Trp, and E is AzaGlyNH$_2$, i.e., NAc-L-Pro-D-p-Cl-Phe-D-Trp-Ser-Tyr-D-Nal(2)-Leu-Arg-Pro-AzaGlyNH$_2$.

18. The compound of claim 2 and the pharmaceutically acceptable salts thereof wherein A is NAc-Pro, B is D-p-F-Phe, C is D-Phe, X is Nal(2) and E is GlyNH$_2$, i.e. NAc-Pro-D-p-F-Phe-D-Phe-Ser-Tyr-D-Nal(2)-Leu-Arg-Pro-GlyNH$_2$.

19. The compound of claim 2 and the pharmaceutically acceptable salts thereof wherein A is NAc-Pro, B is D-p-F-Phe, C is D-Phe, X is Nal(2) and E is AzaGlyNH$_2$, i.e. NAc-Pro-D-p-F-Phe-D-Phe-Ser-Tyr-D-Nal(2)-Leu-Arg-Pro-AzaGlyNH$_2$.

20. The compound of claim 2 and the pharmaceutically acceptable salts thereof wherein A is NAc-Pro, B is D-p-F-Phe, C is D-Phe, X is Nal(2) and E is ProNHEt, i.e., NAc-Pro-D-p-F-Phe-D-Phe-Ser-Tyr-D-Nal(2)-Leu-Arg-Pro-ProNHEt.

21. The compound of claim 1 and the pharmaceutically acceptable salts thereof wherein A is NAc-Pro, B is D-p-Cl-Phe, C is D-Phe, X is Nal(2) and E is GlyNH$_2$, i.e. NAc-Pro-D-p-Cl-Phe-D-Phe-Ser-Tyr-D-Nal(2)-Leu-Arg-Pro-GlyNH$_2$.

22. The compound of claim 1 and the pharmaceutically acceptable salts thereof wherein A is NAc-Pro, B is D-p-Cl-Phe, C is D-Phe, X is Nal(2) and E is AzaGlyNH$_2$, i.e. NAc-Pro-D-p-Cl-Phe-D-Phe-Ser-Tyr-D-Nal(2)-Leu-ArgPro-AzaGlyNH$_2$.

23. The compound of claim 1 and the pharmaceutically acceptable salts thereof wherein A is NAc-Pro, B is D-p-Cl-Phe, C is D-Phe, X is Nal(2) and E is ProNHEt, i.e., NAc-Pro-D-p-Cl-Phe-D-Phe-Ser-Tyr-D-Nal(2)-Leu-Arg-Pro-ProNHEt.

24. A method of inhibiting ovulation in a female mammalian subject, which method comprises administering to said subject an effective amount of the compound of claim 2 or a pharmaceutical composition containing same.

25. A method of treating endometriosis in a female mammalian subject, which method comprises administering to said subject an effective amount of the compound of claim 1 or a pharmaceutical composition containing same.

26. A method of treating prostatic hypertrophy in a male mammalian subject, which method comprises administering to said subject an effective amount of the compound of claim 1 or a pharmaceutical composition containing same.

27. A method of inhibiting spermatogenesis in a male mammalian subject, which method comprises administering to said subject an effective amount of the compound of claim 1 or a pharmaceutical composition containing same.

28. A pharmaceutical composition for inhibiting of ovulation or for treating endometriosis in a female mammalian subject and for treating prostatic hypertrophy or inhibiting spermatogenesis in a male mammalian subject comprising an effective amount of the compound of claim 1 in admixture with at least one pharmaceutically acceptable excipient.

* * * * *